United States Patent [19]

Muller

[11] Patent Number: 5,447,535
[45] Date of Patent: Sep. 5, 1995

[54] MAMMARY PROSTHESIS

[76] Inventor: Guy-Henri Muller, 22 Rue Erckmann Chatrian, 67000 Strasbourg, France

[21] Appl. No.: 163,731

[22] Filed: Dec. 9, 1993

Related U.S. Application Data

[63] Continuation of Ser. No. 581,166, Sep. 5, 1990, abandoned, which is a continuation of Ser. No. 339,713, Apr. 18, 1989, abandoned.

[30] Foreign Application Priority Data

Apr. 27, 1988 [FR] France .................. 8805843

[51] Int. Cl.⁶ ......................................... A61F 2/12
[52] U.S. Cl. ................................... 623/8; 623/11
[58] Field of Search ............ 623/1, 11, 12, 66, 7, 623/8

[56] References Cited

U.S. PATENT DOCUMENTS

| | | | |
|---|---|---|---|
| 2,542,619 | 2/1951 | Bernhardt | 623/7 |
| 3,559,214 | 2/1971 | Pangman | 623/8 |
| 4,205,401 | 6/1980 | Frisch | 623/8 |
| 4,263,682 | 4/1981 | Bejarano | 623/8 |
| 4,428,082 | 1/1984 | Naficy | 623/8 |
| 4,507,810 | 4/1985 | Bantholdsow | 623/8 |
| 4,574,780 | 3/1986 | Manders | 623/8 |
| 4,605,412 | 8/1986 | LaForest et al. | 623/8 |
| 4,650,487 | 3/1987 | Chaglassian | 623/8 |
| 4,790,848 | 12/1988 | Cronin | 623/8 |

*Primary Examiner*—David Isabella
*Attorney, Agent, or Firm*—Popham, Haik, Schnobrich & Kaufman, Ltd.

[57] ABSTRACT

A prosthetic implant comprising a first membrane defining a first compartment and a second membrane, spaced inwardly from the first membrane, defining a second compartment contained within the first compartment. The second compartment is filled with a constantly adjustable amount of fluid. A distinctive unit, situated between the first and second membranes, is filled with a number of individual microcapsules which contain closed volumes smaller than 1 cc of fluid. The microcapsules optionally may be united together by a silicone adhesive. The small volumes avoid leakage of significant amounts of fluid during puncture of the prosthesis to inject or remove fluid subsequent to implantation.

17 Claims, 1 Drawing Sheet

MAMMARY PROSTHESIS

This application is a Continuation of U.S. patent application Ser. No. 07/581,166, filed Sep. 5, 1990, now abandoned, which is a continuation of U.S. patent application Ser. 07/339,713, filed Apr. 18, 1989, now abandoned.

TECHNICAL FIELD

This invention relates to a new prosthetic structure adapted to be inserted or implanted in various regions of the human body to fill in irregularities, to increase the volume and/or to modify the appearance of a given region(s).

BACKGROUND

A typical application of such prostheses is mammoplasty by insertion of mammary implants, and the following description will be directed to such an application., it being understood that this description is intended as a non-limiting example.

It is well-known that present mammary prostheses are generally made of a shell comprising flexible silicone film having a spherical shape more or less flattened and filled with a silicone gel, physiological salt solution, or both.

The drawbacks of using silicone filling gel include the risk of gel leakage through the film shell, either by transudation or even by tearing, with local or even general complications.

The drawbacks of using a physiological filling solution also include the risk of leakage either by tearing of the film or at the filling valve. In both cases mentioned above, there are no physiological consequences, but there occurs a decrease in volume unavoidable after some time and always unaesthetic, often requiring a new surgical operation.

To prevent such drawbacks, there have been attempts to use prostheses comprising a central portion made of silicone gel and a peripheral portion filled with physiological solution ostensibly to oppose gel transudation. However, such composite prostheses may suffer from the drawbacks of both above-mentioned devices.

Prostheses have also been more recently proposed comprising means for providing progressive expansion by serial injection of saline solution through a filling valve in-situ over a period of time, to obtain tissue expansion. In addition to the above drawbacks, this recent process involves several interventions in order to obtain a long term implant or to remove the filling valve.

It should also be kept in mind that the insertion of an implant into living tissue may cause spontaneous creation around the implant of an exclusion membrane, which can retract. This is known as "capsular contracture" and in some cases, specifically mammary implants, the formation of such a hard capsule can only be remedied surgically.

Thus, there is still a need to eliminate the above drawbacks, by avoiding the use of silicone gel and aiding in the prevention of leakage or loss of physiological solution from an implant. There also is a further need to provide an opportunity to modify the volume of the implant, at will, without surgical intervention.

SUMMARY OF THE INVENTION

According to the invention, a silicone envelope is filled with a number of small individual closed volumes, i.e., microcapsules, each formed of a thin silicone membrane and filled with a fluid such as air or other biocompatible gas or liquid, or physiological salt solution. These small closed volumes are distributed around a central volume, which is also enclosed by a silicone membrane and filled with a constantly adjustable amount of physiological solution.

According to a particular embodiment of this invention, the number of small volumes can each comprise a silicone foam with closed alveoles. Although it is more difficult to fill such alveoles, it can still be accomplished by: polymerization of the foam in an aqueous medium; dipping the already polymerized foam into an aqueous medium under very high pressure;, or any other means keeping the alveoles closed.

Preferably, the central volume is made of two hemispheres, i.e., an upper hemisphere having a self-sealing, needle-penetrable wall, e.g. a thick silicone film or any anti-leakage material, and a lower hemisphere made of extensible silicone film to allow volume variation of the implant. To allow for change in the amount of solution in the central volume, the peripheral membrane of the implant comprises at least one thicker portion which is self-sealing after being punctured by a needle used to introduce fluid into or extract it from the central volume during the operation.

According to a further embodiment of the invention, the entire peripheral membrane of the implant can be made of a self-sealing flexible silicone film, to allow expansion of the overall volume when the central volume is filled.

In a further embodiment of the invention, the peripheral membrane of the implant can comprise at least one rigidified portion, e.g., of thick bands of silicone, to give to the filled volume a shape flatter than a, perfect sphere, due to the obtained resistance of the thickened portion to lateral pressure.

The small individual and hermetic volumes filling the peripheral shell around the central volume constitute a distinctive unit from which the contents cannot be readily drained. When the individual volumes are each filled with physiological solution, this unit is incompressible; when the individual units are filled with air, the unit is somewhat "elastic". In both cases, substantial loss of fluid from the unit is prevented from occurring during subsequent injections.

An advantage of this feature is that, although a needle reaching the central volume may puncture some of the individual smaller volumes, the resulting loss from the unit (and hence the implant) is insignificant because the individual volumes are also small.

According to the invention, each of the individual volumes should be as small as possible, preferably smaller than 1 cc. From this point of view, the use of micro-capsules well-known in the carbonless paper arts, as well as in the pharmaceutical field, is contemplated.

BRIEF DESCRIPTION OF THE DRAWING

The invention will now be described with reference to the accompanying drawing wherein.

DETAILED DESCRIPTION

Figure 1:
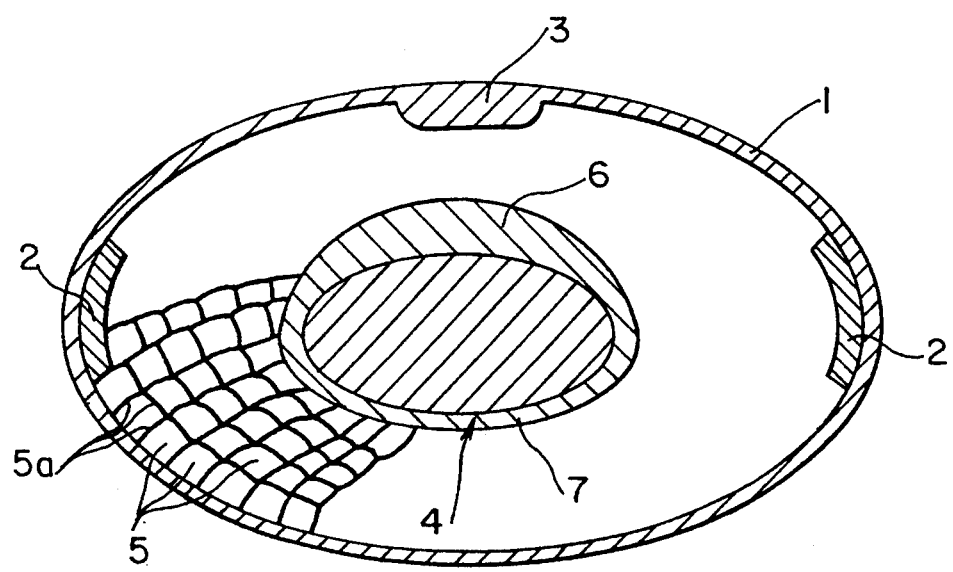
FIG. 1 is a cross-sectional view of a mammary prosthesis of this invention.

Referring to FIG. 1, a mammary implant is generally shown which comprises a peripheral shell 1, for example, a silicone membrane or film, delimiting the structure of the implant. The shell 1 is comparatively thin, (1 to 5 mm) flexible and of variable shape. The shell 1 comprises equatorial portions 2, which are comparatively thicker (5 to 10 mm) than the remaining shell, to give to the equatorial portions 2 a certain rigidity which imparts a flattened spheroidal shape to the implant structure. The shell 1 comprises also a filling portion 3, substantially thicker (2 to 5 mm) than the remaining shell, for penetration by a needle (not shown) to inject or extract physiological solution from the implant.

In the center of the volume delimited by the shell 1 is a central volume 4 defined by a wall which is similar to the above portion 3.

According to a preferred modification, the central volume 4 comprises an upper portion 6 provided with a thickness which can be punctured by an injection needle and be self-sealing. The central volume 4 has a lower portion 7 which is relatively thinner than the upper portion 6 to be extensible for allowing the implant to take an optional volume and shape.

Referring again to FIG. 1, located between the peripheral membrane shell 1 and the central volume 4 is a distinctive unit filled with a great number of small individual closed volumes, i.e., microcapsules 5. Each of the small volumes are hermetically delimited by a thin membrane (0.1 to 1 mm.) and filled by a bio-compatible fluid, such as air, physiological solution or any other bio-compatible gas or liquid medium. These volumes should be as small as possible, preferably less than 1 cc and still more preferably less than 1 mm, this size depending on the filling process, as explained above.

To ensure operational cohesion of the above unit with the central volume, the membranes defining the individual small volumes are preferably coated with an adhesive, such as a silicone elastomeric adhesive or other fixative, to stick one to another.

The advantages of the novel prosthesis structure of the invention are clear, although even further improvements may be obtained by various modifications.

For example, where the shell 1 accidentally ruptures or tears, or where the shell 1 is not self-sealing after penetration by the filling or extraction needle, only the small volumes of those individual cells that were punctured are emptied while the remaining untouched volumes retain their shape and volume. The well-known disadvantage of "waves", displayed by usual mammary prostheses, is therefore prevented.

The central volume 4 displays several features, discussed below.

First, it is possible to adapt the volume of the implant during and after the initial surgical intervention, by simply punching the filling needle through the implant to inject or extract the desired amount of physiological solution from the central volume 4. During a surgical operation, the volume of the prosthesis can be adapted to any desired amount, starting from a given initial volume. After the operation, it is possible to fill or empty the central volume 4 by injection through the breast to effect the desired shape.

Thus, it is possible with the invention to modify the volume without any new surgical intervention. Specifically, it is possible to overfill a prosthesis at the moment of surgical implantation, then decrease the volume some weeks later, in order to oppose the capsular contracture phenomenon. If the tissue capsule appears at a later stage, the prosthesis may be subsequently expanded through transcutaneous injection until contracture ceases and the prosthesis volume can then be decreased, without any surgical intervention being performed.

The prosthesis may also be used as a tissue expander without valve, where mammary reconstruction of a new breast is attempted by distension and new growth of the thoracic skin. In this procedure, the implant is distended by transcutaneous needle insertion. Then, when the cutaneous state is found satisfactory, a further fluid injection allows adjustment of mammary volume, without further surgery.

In another aspect of the invention, the central volume 4 can be provided with several peripheral compartments, dividing the spheroidal implant into several portions which can be independently filled or emptied. An advantage of this feature is an accommodation of specific thoracic distortions by distension of a corresponding portion of the implant, for example, the lower portion, in the course of mammary reconstruction.

According to a further aspect of the invention, the peripheral compartment can be provided with external "facets" which swell when the compartment is pressurized by injection of physiological solution. These facets give rise to discontinuities in the peripheral shell implant wall, which minimize the possibility of contracture of the periprosthetic capsule. This peripheral compartment can be swollen during implantation of the prosthesis and then emptied or further swollen by subsequent injection.

The general shape of the implants according to the invention can be different depending on the area of the body where they must be inserted, i.e., breast, legs, chin, scalp, etc. In each of these bodily areas, the new implant keeps its significant feature of adaptability without further surgical intervention.

In the commercial use of this new product, caution should be exercised to prevent any dehydration of the product. Rather, the product should be presented in an aqueous medium, such as a bag of physiological solution, for use as an introduction system, thereby preventing any direct contact with the surgeon's hands.

What is claimed is:

1. A prosthetic implant comprising:
   a first flexible membrane defining a first closed compartment;
   a second flexible membrane, spaced inwardly from the first membrane and enclosing a second closed compartment which is contained within the first compartment, the second compartment being filled with a continuously-adjustable amount of bio-compatible fluid; and
   a distinctive intermediate unit, disposed within a peripheral space defined between the first and second membranes, the unit comprising individual closed microcapsules each containing a small closed volume of less than 1 cc of bio-compatible fluid.

2. The implant of claim 1 wherein at least one of the first and second membranes comprises a silicone membrane.

3. The implant of claim 1 wherein the bio-compatible fluid comprises a physiological salt solution.

4. The implant of claim 1 wherein the first membrane further comprises stiffened portions for imparting a non-spherical shape to the implant when the first volume becomes swollen.

5. The implant of claim 4 wherein the stiffened portions further comprise at least one zone of increased thickness which is self-sealing following puncture by an injection needle.

6. The implant of claim 5 wherein the zone of increased thickness further comprises at least one piece of silicone film.

7. The implant of claim 1 wherein each of the microcapsules further comprises an encapsulating membrane coated with an adhesive which causes the microcapsules to be cohesive with one another and with the second membrane.

8. The implant of claim 1 further comprise a third membrane defining a third volume which may be independently expanded and contracted.

9. The implant of claim 8 wherein the third volume further comprises an external facet projecting from the first membrane.

10. The implant of claim 1 wherein the second compartment comprises an upper hemisphere and a lower hemisphere, the upper hemisphere comprising a relatively thick silicone film which is punchable and self-sealing, and the lower hemisphere comprising an extensible silicone film adapted to distend the shape of the implant.

11. The implant of claim 1 wherein the microcapsules further comprise a silicone foam having closed alveoles.

12. An implantable mammary prosthesis comprising:
a first flexible silicone membrane defining a first closed compartment;
a second flexible membrane having an upper hemisphere with a thick silicone film punchable and self-sealing and a lower hemisphere made of extensible silicone film adapted to distend the shape of the implant, the second membrane being spaced inwardly from the first membrane and enclosing a second compartment which is contained within the first compartment, the second compartment being filled with a continuously-adjustable amount of physiological salt solution; and
a distinctive intermediate unit, disposed within a peripheral space defined between the first and second membranes, the unit being filled with individual closed microcapsules each containing a small closed volume of less than 1 cc of physiological salt solution and being glued together with a silicone adhesive.

13. The implant of claim 1, wherein the first membrane further comprises a thickened portion having the property of self-closing after punching by a needle used for introducing or extracting physiological solution into or from the first compartment to modify the overall volume of the implant.

14. A prosthetic implant comprising:
a flexible membrane defining a closed compartment filled with a continuously-adjustable amount of bio-compatible fluid contained within a plurality of individual closed cells each containing a small closed volume of less than 1 cc of the bio-compatible fluid, whereby no visible or tactile irregularities are presented and only minimal loss of fluid is allowed upon puncture.

15. The implant of claim 14 wherein the membrane comprises a silicone elastomer.

16. The implant of claim 15 wherein the bio-compatible fluid comprises a physiological salt solution.

17. The implant of claim 14 wherein the cells have an average volume less than 1 cc.

* * * * *